United States Patent [19]

DeVries et al.

[11] Patent Number: 5,243,068

[45] Date of Patent: Sep. 7, 1993

[54] PROCESS FOR PREPARING VINYLICALLY-UNSATURATED COMPOUNDS (II)

[75] Inventors: Robert A. DeVries, Midland; Hughie R. Frick, deceased, late of Midland, both of Mich., by Bonnie Frick, administrator

[73] Assignee: The Dow Chemical Company, Midland, Mich.

[21] Appl. No.: 877,580

[22] Filed: May 1, 1992

Related U.S. Application Data

[62] Division of Ser. No. 676,622, Mar. 28, 1991, Pat. No. 5,136,069.

[51] Int. Cl.⁵ .......................... C07C 69/52; C07C 1/00
[52] U.S. Cl. ..................... 560/205; 585/641; 585/642
[58] Field of Search ................ 560/205; 585/514, 641, 585/642

[56] References Cited

PUBLICATIONS

Yamamoto, "Organotransition Metal Chemistry", 1986 pp. 383-386.

March, "Advanced Organic Chemistry", 3rd Ed. 1985, p. 895.
Carey et al. "Advanced Organic Chemistry", Part B 2nd ED. pp. 285-291.

Primary Examiner—José G. Dees
Assistant Examiner—Joseph M. Conrad
Attorney, Agent, or Firm—Charlotte M. Kraebel; Charles J. Enright

[57] ABSTRACT

A process for preparing a vinylically-unsaturated product compound comprises reacting a halogenated organic compound with a hydrolytically-stable, vinylically-unsaturated precursor compound in the presence of (a) a homogeneous zerovalent palladium catalyst complex, (b) an inorganic hydrogen halide acceptor and (c) a diluent, wherein the diluent is water or an aqueous solution containing up to 95% by volume of an organic solvent. The halogenated organic compound is selected from aryl halides, benzyl halides or vinylic halides. The hydrolytically-stable, vinylically-unsaturated precursor compound is selected from hydrocarbon compounds or compounds containing at least one of an oxygen atom, a nitrogen atom, a sulfur atom, a phosphorus atom or a combination thereof.

40 Claims, No Drawings

PROCESS FOR PREPARING VINYLICALLY-UNSATURATED COMPOUNDS (II)

CROSS REFERENCE TO RELATED APPLICATION

This is a divisional of application Ser. No. 676,622 filed Mar. 28, 1991, now U.S. Pat. No. 5,136,069.

TECHNICAL FIELD

This invention relates to an improved process for the synthesis of vinylically-unsaturated compounds by reaction between halogenated organic compounds and hydrolytically-stable, vinylically-unsaturated precursor compounds.

BACKGROUND ART

The palladium-catalyzed vinylation of organic halides has been reviewed by Heck, *Organic Reactions*, vol. 27 (1982), beginning at page 345. Process conditions, recited at page 360, do not require the use of a solvent, although an organic amine can apparently function as a solvent. Other solvents used heretofore include acetonitrile, methanol, dimethylformamide, N-methylpyrrolidinone and hexamethyl phosphoramide.

Heck, U.S. Pat. No. 3,922,299, incorporated herein by reference, teaches that the reaction can be carried out with or without a solvent. Suggested solvents include acetonitrile, tetrahydrofuran or excess olefin.

The Heck vinylation reaction has been used to vinylate various kinds of compounds, including vinylation using vinylically-unsaturated organosilicon compounds. The preparation of polysiloxane-bridged bisbenzocyclobutene monomers has been recited by Gros, U.S. Pat. No. 4,759,874, and Schrock, U.S. Pat. No. 4,812,588, both herein incorporated by reference. Other silane-containing compounds have been synthesized by Hahn et al., U.S. Pat. No. 4,831,172, herein incorporated by reference. Similar synthesis of benzocyclobutene compounds is disclosed by Kirchhoff, U.S. Pat. No. 4,540,763, herein incorporated by reference.

Known processes for reaction between halogenated organic compounds and hydrolytically-stable, vinylically-unsaturated precursor compounds have been carried out in organic solvents.

It has surprisingly been found that the Heck-type vinylation reaction can be carried out in aqueous media, including aqueous solutions of organic solvents.

It is therefore the object of this invention to provide an improved process for vinylation of halogenated organic compounds, wherein an aqueous diluent is used.

DISCLOSURE OF INVENTION

This invention relates to a process for preparing a vinylically-unsaturated product compound, comprising reacting a halogenated organic compound with a hydrolytically-stable vinylically-unsaturated precursor compound selected from the group consisting of (i) hydrocarbons and (ii) compounds containing one or more of an oxygen atom, a nitrogen atom, a sulfur atom, a phosphorus atom, or a combination thereof, in the presence of (a) a homogeneous zerovalent palladium catalyst complex, (b) an inorganic hydrogen halide acceptor and (c) a diluent, wherein the diluent is water or an aqueous solution containing up to 95% by volume of an organic solvent.

This invention further relates to a process for preparing a vinylically-unsaturated organosilicon product compound, comprising reacting a halogenated organic compound with a hydrolytically-stable allyl, methallyl or vinyl organosilicon precursor compound in the presence of (a) a homogeneous zerovalent catalyst complex, formed from a palladium salt and an organophosphine or organoarsine; (b) an inorganic hydrogen halide acceptor and (c) a diluent comprising water or an aqueous solution, containing up to 95% by volume of an organic solvent; and treating a resulting crude product mixture with an organic peroxide to remove organophosphine or organoarsine present in the mixture.

DETAILED DESCRIPTION OF THE INVENTION

The reaction between halogenated organic compounds and hydrolytically-stable, vinylically-unsaturated precursor compounds is carried out in the presence of a zerovalent palladium catalyst complex. The catalyst complex can be added to the reaction mixture or can be formed in the reaction mixture. Representative preformed catalyst complexes include tetrakis-(triphenylphospine)palladium (0), tris(dibenzylideneacetone)dipalladium (0) with triphenylphosphine and dichloro-(triphenylphosphine)palladium (II).

The catalyst complex can be prepared in the reaction mixture, generally by reaction between a palladium (II) compound and a trivalent organophosphorus or organoarsenic compound.

The reaction between the vinylically-unsaturated precursor compound and halogenated organic compound, in the presence of a representative palladium complex, can be represented by the general equation:

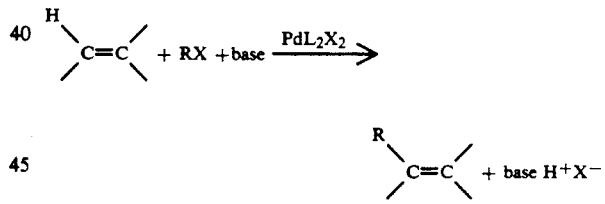

wherein R is aryl, heterocyclic, vinylic or benzyl and X is bromo, iodo or, rarely, chloro. L represents a ligand, which is a trivalent organophsphorus or organoarsenic compound. The base in the equation corresponds to the inorganic hydrogen halide acceptor.

Representative ligands in the Pd catalytic complex include, but are not limited to, triphenylarsine, triphenyl arsenite, tri-(n-butyl)phospine, diphenylmethylphosphine, diphenylmethoxyphosphine, trimethyl phosphite, triphenylphosphine, triethylphospine, phenyldi-(n-butoxy)phospine, tris-(p-anisyl)phosphine, tris-(o-tolyl)phospine and tris-(o-totyl) phosphite.

Palladium is introduced into the reaction mixture in the form of a salt, such as the acetate or chloride. It is postulated that the catalyst complex should contain two phosphine or arsine ligands per palladium atom.

Catalysts, or catalytic complexes, formed from palladium (II) acylates, particularly Pd(II) acetate, and triaryl phosphines have been found to be particularly preferred for the practice of this invention. Particularly preferred triaryl phosphines are triphenylphosphine and tris-(o-tolyl)phosphine.

Most preferred catalysts are those obtained from Pd (II) acetate and tris-(o-tolyl)phosphine.

The ratio of palladium (II) compound to phosphorus or arsenic ligand can be varied from about 1:1 to about 1:100. It is preferred to operate at ratios of from about 1:2 to about 1:10, particularly when a catalyst from Pd (II) acetate and tris-(o-tolyl)phosphine is used.

The amount of catalyst complex is varied from about 0.1 mol to 0.00001 mol (as Pd) per mol of halogenated organic compound in the reaction mixture. Preferably, the catalyst level is 0.01–0.00001 mol (as Pd) per mol of halogenated organic compound.

The inorganic hydrogen halide acceptor is selected from salts of weak acids and strong bases or corresponding oxides or hydroxides, particularly of the Group I alkali metals and Group II alkaline earth metals. Inorganic hydrogen halide acceptors accordingly include salts, oxides and hydroxides of lithium, sodium, potassium, cesium, magnesium, calcium, strontium and barium.

Preferred inorganic hydrogen halide acceptors are selected from alkali metal hydroxides, carbonates and acylates, particularly acetates or propionates. Most preferred are sodium or potassium acetate.

The molar ratio of inorganic hydrogen halide acceptor to halogenated organic compound can be varied from about 1:1 to about 10:1. Using greater excesses of inorganic hydrogen halide acceptor is not particularly advantageous. It has, surprisingly, been found that excellent results are obtained using 1.5–2:1 molar ratios of inorganic hydrogen halide acceptor to halogenated organic compound. Therefore, preferred ratios of inorganic hydrogen halide acceptor to halogenated organic compound are from about 1:1 to about 2:1.

The optional organic hydrogen halide acceptor, used in the practice of this invention, is a secondary or tertiary amine. Representative organic hydrogen halide acceptors include, but are not limited to, trimethylamine, triethylamine, methylethylamine, diethyl-n-butylamine, triisobutylamine, tri-n-butylamine, diisopropylamine, triisopropylamine, N,N,N',N'-tetramethylethylene diamine, N-methylcyclohexylamine, N,N-diethylcyclohexylamine, N,N-diethylaniline, N,N-dimethylaniline, N-methyltoluidine, pyridine, quinoline, the lutidines, N-methylpiperidine, N-methylpyrrole and the like.

Preferred optional organic hydrogen halide acceptors are tertiary amines, particularly those represented by the formula $R_1R_2R_3N$, wherein each of $R_1$, $R_2$ and $R_3$ is selected independently from straight-chain and branched-chain alkyl of 1–8 carbon atoms and cycloalkyl. Most preferably, the optional organic hydrogen halide acceptor is triethylamine.

The amount of optional organic hydrogen halide acceptor used is normally 0.5–2.5 moles per mol of inorganic hydrogen halide acceptor. It is frequently preferred, owing to flammability, odor, cost and environmentally objectionable properties of organic hydrogen halide acceptors, to use no organic hydrogen halide acceptor in the process of this invention.

The diluent can be water or an aqueous solution, containing up to 95% by volume of an organic solvent. When water is used as the diluent, the amount of water preferably exceeds 50% by weight of the combined organic reactants. Combined organic reactants means the combined weights of halogenated organic compound and hydrolytically-stable, vinilically-unsaturated precursor compound. More preferably, the amount of water exceeds 100% by weight of the combined organic reactants. Preferably, the amount of water is less than 500% by weight of the combined organic reactants. The amount of water is selected, within these limits, so as to be sufficient to dissolve the hydrohalide salt, formed during the reaction. Use of an amount of water, sufficient to dissolve salts formed by the reaction, greatly facilitates isolation and purification of the reaction products.

The use of an aqueous solvent in the process does not adversely affect the yield or product distribution. Use of a diluent, containing significant amounts of water prevents formation of intractable salt accumulations in the reactor and on the stirrer. A reaction medium, from which by products do not accumulate on the walls of the reactor or stirrer, permits more efficient heat transfer and better agitation than possible when salt-cake formation occurs.

In some cases, phase separation into an aqueous salt-containing layer and an organic product-containing layer occurs. Separation of the reaction mixture into a two-phase system is very desirable and facilitates removing the by-product salt and isolating the desired product from the organic phase.

Aqueous solvents, used as diluents, preferably contain up to 90% by volume of an organic solvent. Organic solvents can be selected from nitriles, alcohols, ketones, linear or cyclic saturated esters, N,N-dialkylformamides, N-alkylpyrrolidinones, alkoxyalkanols, glycol ethers, dioxane, tetrahydrofuran, tetrahydropyran or hexaalkylphosphoramides. It will be understood that the foregoing organic solvents are representative of water-miscible solvents, acceptable for use in the process of this invention.

Suitable nitriles include, but are not limited to, acetonitrile, propionitrile, butyronitrile, and higher aliphatic nitriles, as well as benzonitrile, tolylnitrile, methoxybenzonitrile, etc. A preferred nitrile solvent is acetonitrile.

Alcohols which can be used in the aqueous diluent solutions include alkanols of 1–8 carbon atoms, including the various isomeric forms.

Esters useful in aqueous diluent solutions include linear or cyclic saturated esters, for example, ethyl acetate, methyl propionate, isopropyl butyrate, caprolactone and butyrolactone.

Ketones, useful in the aqueous diluent solutions, include acetone, methyl ethyl ketone, methyl isopropyl ketone, and similar compounds.

Of the various N,N-dialkylformamides which can be used in the aqueous diluent, N,N-dimethylformamide is most preferred.

N-Methylpyrrolidinone is preferred among the various N-alkylpyrrolidinones.

Alkoxyalkanols suitable for use in aqueous diluents include those of up to about 10 carbon atoms, e.g. ethylene glycol monomethyl ether, propylene glycol monoethyl ether, ethylene glycol monobutyl ether, propylene glycol monoisopropyl ether, etc.

Glycol ethers, including ethylene glycol dimethyl or diethyl ethers, corresponding propylene glycol ethers, or diethylene glycol or triethylene glycol diethers can also be used.

Of the hexaalkylphosphoramides which can be used in the aqueous diluents, hexamethylphosphoramide is preferred.

Preferred aqueous diluents are those containing 10–90% by volume of N,N-dimethylformamide or N-methylpyrrolidinone. Most preferred diluents are aqueous solutions containing 30–70% by volume of dimethylformamide or N-methylpyrrolidinone.

Most preferably, the process of this invention is one wherein the diluent is an aqueous solution of 30–70% by volume of N,N-dimethylformamide or N-methylpyrrolidinone and the diluent is present in an amount equal to at least 70% by weight of combined halogenated organic compound and hydrolytically-stable, vinylically-unsaturated precursor compound.

Halogenated organic compounds, useful as starting materials for the process of this invention, include mono- and polycyclic, substituted or unsubstituted carbocyclic or heterocyclic aromatic bromo and iodo compounds and, rarely, chloro compounds. Aryl iodides may react in the presence of Pd (0), without a phosphine or arsine ligand. The reactive halogenated organic compounds can be classified broadly as aryl halides, benzyl halides or vinylic organic halides. It will be understood that selection of halogenated aromatic compounds is limited to those which are inert to undesired side reactions under the reaction conditions used and that this can be determined by routine experimentation.

Benzyl halides include substituted and unsubstituted benzyl chlorides, bromides and iodides. The benzyl chlorides are sufficiently reactive to add to a vinylically-unsaturated precursor compound. Benzyl chlorides and halides are preferred reagents for this synthesis. Substituents on the aromatic ring of the starting benzyl halide straight and branched chain alkyl, alkoxy, nitro, cyano, hydroxy, keto, amide, carboxy, dialkylamino and sulfone groups. It will be understood that 1-halobenzocyclobutenes represent a type of benzyl halide.

Vinylic halides, useful in the practice of this invention include, for example, 1- or 2-bromoalkenes or 1- or 2-iodoalkenes of the formulas $CH_2=CXR$ or $CHX=CHR$, wherein R is alkyl or aryl and X is Br or I.

Aromatic halides include substituted and unsubstituted aryl bromides and iodides. Aryl chlorides generally are unreative under the conditions used. Substituents on the aromatic ring or rings can include straight and branched chain alkyl, alkoxy, nitro, cyano, hydroxy, ketone, amide, carboxy, dialkylamino or sulfone groups. Aromatic halides include both monocyclic and polycyclic aromatic halides.

Representative heterocyclic reactants include, but are not limited to, bromofuran, bromopyridine, bromo-N-methylpyrrole, iodofuran, iodolutidine, etc.

Preferably, the halogenated organic compound used as feed is selected from bromo- or iodo- mono- or polycyclic substituted or unsubstituted carbocyclic or heterocyclic compounds or substituted or unsubstituted benzyl chlorides or bromides. Bromo compounds are most preferred as starting materials.

Substituents on substituted halogenated carbocyclic aromatic compounds are preferably selected from alkyl of 1–6 carbon atoms, alkoxy of 1–6 carbon atoms, chloro or cyano. It will be appreciated that alkyl and alkoxy substituents can be straight-chain or branched-chain.

A class of preferred reactants include bromo- or iodobenzocyclobutenes, as disclosed by Gros, U.S. Pat. No. 4,759,874, supra. Most preferably, the reactant is a brominated benzocyclobutene, represented by the formula

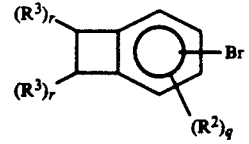

wherein $R^2$ is alkyl of 1–6 carbon atoms, acyloxy of 1–6 carbon atoms, alkoxy of 1–6 carbon atoms, nitro or chloro; each $R^3$ is independently alkyl of 1–6 carbon atoms, aryl, nitro, chloro or cyano; q is 0, 1, 2 or 3 and each r is independently 0 or 1.

Brominated benzocyclobutenes can be prepared as recited by Liu, U.S. Pat. No. 4,822,930, herein incorporated by reference. Most preferably, 4-bromobenzocyclobutene is used in processes of this invention. This starting material is obtained in high purity by distilling materials in accordance with Liu '930.

It will be understood that "benzocyclobutene" is an art-recognized term for a cyclobutarene compound, Liu '930. Cyclobutarene compounds are compounds, containing at least one aromatic ring, which is fused to one or more substituted or unsubstituted cyclobutene ring. An aromatic ring contains (4N+2)n electrons, as described in Morrison and Boyd, *Organic Chemistry*, third edition (1973). In the numbering system for benzocyclobutenes, the 1- and 2-positions are in the cyclobutene ring. The 3- and 6-positions are in an aromatic ring, adjacent to the cyclobutene ring. The 4- and 5-positions are meta- to the cyclobutene ring. Benzocyclobutenes are formally identified as derivatives of bicyclo[4.2.0] octa-1,3,5-triene. Correlations between various representative names and structures are given in Table 1.

Preferred halogenated organic compounds include brominated and iodinated alkylbenzenes and alkylnaphthalenes or corresponding alkoxy compounds, wherein alkyl and alkoxy are of 1–6 carbon atoms and can be of any isomeric structure. A particularly preferred halogenated organic compound is of the formula ArBr, wherein Ar is substituted or unsubstituted monocyclic aromatic. Most preferred as a halogenated organic compound is that wherein Ar is phenyl or o-, m- or p-tolyl, or a mixture thereof. The use of o-alkylbromobenzenes, which react with various olefins to provide a feasible process for making hitherto hard-to-synthesize o-vinylalkylbenzenes, is particularly preferred.

Also preferred as halogenated organic compounds are substituted or unsubstituted benzyl chlorides or bromides, particularly those wherein the substituent is alkyl or alkoxy of 1–6 carbon atoms.

Vinylic iodides or bromides are also preferred.

Hydrolytically-stable, vinylically-unsaturated precursor compounds employed in the process of this invention can be selected from three general classes of compounds:

(a) hydrocarbon compounds, including vinyl, allyl and methallyl hydrocarbons, of various degrees of substitution;

TABLE 1

Structures and Names of Representative Reactants and Products

| Short Name | Structure | Alternative Names |
|---|---|---|
| 4-BrBCB | Br—⟨benzocyclobutene⟩ | 3-bromobicyclo[4.2.0]octa-1,3,5-triene<br>4-bromobenzocyclobutene |
| DVS | [H$_2$C=CHSi(CH$_3$)$_2$]$_2$O | 1,1'-divinyltetramethyldisiloxane<br>1,3-divinyltetramethyldisiloxane |
| BCB—VT | 4-BCBCH=CHC$_6$H$_4$CH$_3$ | [(4-benzocyclobutenyl)vinyl]toluene<br>3-[2-(methylphenyl)ethenyl]bicyclo[4.2.0]octa-1,3,5-triene |
| DVB-bis-BCB | (4-BCB—CH=CH)$_2$C$_6$H$_4$ | bis-[(4-benzocyclobutenyl)vinyl]benzene |
| DVS—BCB$_2$ | [(4-BCB—CH=CH)—Si(CH$_3$)$_2$]$_2$O | 1,1'-bis-[(4-benzocyclobutenyl)vinyl]tetramethyldisiloxane<br>1,3-bis-(2-bicyclo[4.2.0]octa-1,3,5-trien-3-yl-ethenyl)-1,1,3,3-tetramethyldisiloxane |
| vinyl-BCB | 4-BCB—CH=CH$_2$ | 4-vinylbenzocyclobutene<br>3-ethenyl-bicyclo[4.2.0]octa-1,3,5-triene |
| bis-BCB-ethylene | 4-BCB—CH=CH—BCB-4 | 1,2-bis-(4-benzocyclobutenyl)ethylene<br>3,3'-(1,2-ethenediyl)bicbicyclo[4.2.0]octa-1,3,5-triene |
| DVS—BCB | 4-BCB—CH=CH—Si(CH$_3$)$_2$OSi(CH$_3$)$_2$CH=CH$_2$ | 1-[(4-benzocyclobutenyl)vinyl]-1'-vinyltetramethyldisiloxane |

4-BCB— = 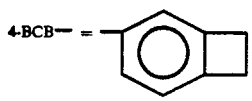

(b) compounds containing vinyl, allyl or methallyl moieties and one or more of oxygen, nitrogen, phosphorus or sulfur atoms, or a combination thereof; and (c) vinyl, allyl or methallyl organosilicon compounds.

Hydrocarbon hydrolytically-stable, vinylically-unsaturated precursor compounds useful in the process of this invention include compounds having a vinyl, allyl or methallyl function, whether substituted or unsubstituted by another hydrocarbon function. Compounds containing a plurality of vinyl, allyl or methallyl functions can be used, including those wherein the unsaturated bonds are conjugated. Representative hydrolytically-stable, vinylically-unsaturated hydrocarbon compounds for the purposes of this invention include, but are not limited to, ethylene, propylene, 1-butene, 2-butene, 2-methyl-1-propene, 1,3-butadiene, 2-methyl-1,3-butadiene, 1,4-pentadiene, 1,5-hexadiene, 3-methyl-1-butene, styrene, substituted styrenes, divinylbenzenes, diallylbenzenes, di(methylallyl)benzenes, 1- and 2-vinylnaphthalene and subsituted vinylnaphthalenes, vinylcyclohexane, stilbene, vinylcyclopentane, allylcyclohexane, methallylcyclohexane and substituted cyclopentanes and cyclohexanes. Substituents include alkyl and aryl groups, e.g., alkyl of 1–6 carbon atoms, phenyl, tolyl, xylyl, etc.

Preferred hydrolytically-stable, vinylically-unsaturated precursor compounds useful as starting materials for the process of this invention include ethylene, styrene, various vinyltoluene or divinylbenzene isomers, including mixtures of isomers.

It will be understood that the process of this invention contemplates stepwise reaction between several moles of halogenated organic compound per mole of hydrolytically-stable, vinylically-unsaturated precursor compound. For example, 4-bromobenzocyclobutene (4-BrBCB) can be reacted with ethylene to produce (4-benzocyclobutenyl)ethylene, 1,2-bis-(4-benzocyclobutenyl)ethylene and 1,1,2-tris-(4-benzocyclobutenyl)ethylene.

Intermediate reaction products, for example, stilbene, can be reacted with additional halogenated organic compounds. Stilbene can be reacted with 4-BrBCB to produce 1,2-diphenyl-1-(4-benzocyclobutenyl)ethylene. Reacted with 2-bromotoluene, ethylene could produce o,o'-dimethylstilbene, etc.

Hydrolytically-stable vinylically-unsaturated precursor compounds include those containing as a hetero atom one or more of oxygen, nitrogen, phosphorus or sulfur, or a plurality thereof. These compounds include, but are not limited to acrylate and methacrylate esters, acrolein, methacrolein, ethacrolein, crotonaldehyde, vinyl acetate, vinyl octoate, vinyl propionate, vinyl versatate, vinyl laurate, allyl acetate, methallyl acetate, allyl versatate, methallyl laurate, allyl stearate, nitroethylene, nitropropylene, nitrostyrene, nitro-alpha-methylstyrene isomers, methyl vinyl ether, ethyl vinyl ether, stearyl vinyl ether, isostearyl vinyl ether, allyloxymethane, allyloxymethane, methallyloxypropane, phenyl vinyl ether, allyloxybenzene, acrylonitrile, methacrylonitrile, acrylamide, methacrylamide, N,N-diethylacrylamide, vinyl diethyl phosphite, divinylmethylphosphine, methyl vinyl thioether, etc., vinylphosphonic acid, allylphosphonic acid, etc.

Preferred hydrolytically-stable O, S, N or P compounds include acrylonitrile or methacrylonitrile and further include acrylate or methacrylate esters, wherein the alcohol moiety is alkyl of 1–30 carbon atoms or substituted or unsubstituted mono- or bicyclic aryl.

Organosilicon compounds are commercially available. A representative source is Petrarch Systems, Inc., Bartram Road, Bristol, Pa., 19007 See, example, Petrarch's "Silicon Compounds Register and Review," (1987), page 114, which recites the availability of bis(-dimethylamino)methylvinylsilane, 1-bromovinyltrimethylsilane, tert.-butydimethylvinylsilane, divinyldimethylsilane, 1,3-divinyl-1,3-diphenyl-1,3-dimethyldisilazane, 1,3-divinyl-1,3-diphenyl-1,3-dimethyldisilazane, 1,3-divinyl-1,1,4,4-tetramethyldisilylethylene, phenyldimethylvinylsilane, phenylmethylvinylsilane, polyvinylmethylsiloxane, 1,1,3,3-tetravinyldimethyldisiloxane, tetravinylsilane, 1,3,5,7-tetramethylcyclotetrasiloxane, triphenylvinylsilane, tris(vinyldimethylsiloxy)methylsilane, tris(vinyldimethylsiloxy)methylsilane, trivinylmethylsilane and 1,3,5-trivinyl-1,1,3,5,5-pentamethyltrisiloxane, any of which is exemplary of hydrolytically-stable organosilicon compounds, useful in the practice of this invention. Preferred organosilicon compounds include those containing vinyl, allyl or methallyl function, bonded to silicon. Trialkylvinylsilanes, wherein alkyl is of 1–6 carbon atoms, are preferred.

A further group of preferred organosilicon compounds are di- and higher polysiloxanes, represented by the formula

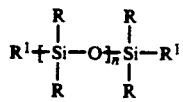

wherein each R is independently alkyl of 1–6 carbon atoms, cycloalkyl, aralkyl or aryl; each $R^1$ is independently vinyl, allyl or methallyl; and n is an integer from 1 to 4500.

Most preferably, $R^1$ os vinyl and each R is methyl, ethyl or phenyl. Preferred siloxanes are those wherein n is 2–10. Several of these compounds are available from Petrarch Systems, above. A most preferred member of this group of compounds is 1,1'-divinyltetramethyldisiloxane, represented by the formula $[CH_2=CHSi(CH_3)_2]_2O$.

Most preferred products, obtained by the process of this invention, are those prepared from:
(a) 4-bromobenzocyclobutene and a mixture of m- and p-vinyltoluene;
(b) 4-bromobenzocyclobutene and divinylbenzene
(c) ethylene and o-bromotoluene
(d) 4-bromobenzocyclobutene and ethylene and
(e) 4-bromobenzocyclobutene and styrene.

The molar ratio of halogenated organic compound to hydrolytically-stable, vinylically-unsaturated precursor compound can be determined by routine experimentation. Generally, molar ratios of about 0.5:1 to 1.5:1 will be preferred for the synthesis of monoadducts. Higher molar ratios of halogenated organic compound to hydrolytically-stable, vinylically-unsaturated precursor will be employed when higher adducts are being prepared.

The temperature at which the process of this invention is performed can be from about room temperature to the temperature at which the starting materials or products decompose or polymerize. Elevated temperatures are normally preferred. It has been found that heating under reflux, generally at 80°–120° C., usually permits a reasonable reaction rate. The temperature conditions for a given set of reactants and diluent can readily be ascertained by routine experimentation.

For certain applications, the compounds prepared by the process of this invention are acceptable, without further purification. For example, reaction products from halogenated aromatic compounds and ethylenically-unsaturated hydrocarbons or compounds containing N, O, S or P can be used without purification more stringent than distillation or crystallization, as may be apparent to a person skilled in the art.

Products with extremely low ionic impurity levels are required when the products are being used, for example, as adhesion promoters for electronic devices. Adhesion promoters must be free of significant levels of phosphorus impurities. It has been found that treating a crude reaction mixture with a peroxide is effective to oxidize phosphine residues to a corresponding phosphine oxide. When organoarsines are used in the catalyst complex, conversion to a corresponding arsine oxide is accomplished in the same way.

Aqueous hydrogen peroxide can be used for this purpose. The crude product is treated with aqueous hydrogen peroxide at ambient or somewhat elevated temperatures for a time sufficient to oxidize residual phosphine to phosphine oxide.

Preferably, oxidation of phosphine residues is done using an organic peroxide. Preferred organic peroxides include hydroperoxides, peresters and peracids, of which tert-butyl hydroperoxide, cumeme hydroperoxide, perbenzoic acid, m-chloroperbenzoic acid, monoperphthalic acid and peracetic acid are representative. tert-Butyl hydroperoxide is preferred. Treatment with an organic peroxide can be done at ambient temperature or at temperatures up to 80°–90° C.

It is preferred to purify the crude reaction products by chromatography over silica gel or alumina. This accomplishes removal of palladium residues and, when used after treatment of a crude product with a peroxide, also removes phosphine oxide.

When ultrapure, ionic-free, reaction products are required, as for adhesion promoters in electronic applications, it is preferred to treat crude reaction products with aqueous hydrogen peroxide or tert-butyl hydroperoxide and to chromatograph the crude products over silica or alumina. These purification steps can be carried out in either order.

The compounds prepared by the process of this invention have a variety of utilities. o-Vinyltoluene is an ethylenically-polymerizable monomer, useful for making resins. Derivatives of benzocyclobutenes polymerize thermally by formation of o-xylylene moities, which can undergo Diels-Alder condensation reactions with mono-enes and provide a route to polymers with high temperature stability. Benzocyclobutenes can also act as crosslinking agents in polymers, as disclosed by Wong (U.S. Pat. No. 4,622,375).

Accordingly, preferred processes of this invention are those wherein:

(a) the halogenated organic compound is a bromo or iodo mono- or polycyclic substituted or unsubstituted carbocyclic or heterocyclic compound or a substituted or unsubstituted benzyl chloride, bromide or iodide;

(b) the halogenated organic compound is a brominated benzocyclobutene represented by the formula

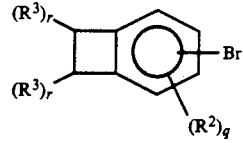

wherein $R^2$ is alkyl of 1–6 carbon atoms, alkoxy of 1–6 carbon atoms, trifluoroacetoxy, acyloxy of 1–6 carbon atoms, nitro or chloro; each $R^3$ is alkyl of 1–6 carbon atoms, aryl, nitro, chloro or cyano; q is 0, 1, 2 or 3 and each r is independently 0 or 1;

(c) the halogenated organic compound is 4-bromobenzocyclobutene;

(d) the halogenated organic compound is of the formula ArBr, wherein Ar is phenyl or o-, m- or p-tolyl;

(e) the halogenated organic compound is a substituted or unsubstituted benzyl bromide or chloride;

(f) the halogenated organic compound is a vinylic bromide;

(g) the hydrolytically-stable, vinylically-unsaturated precursor compound is a hydrocarbon, including each of (a)–(f);

(h) the hydrolytically-stable, vinylically-unsaturated precursor compound is ethylene, including each of (a)–(f);

(i) the hydrolytically-stable, vinylically-unsaturated precursor compound is styrene, including each of (a)–(f);

(j) the hydrolytically-stable, vinylically-unsaturated precursor compound is o-, m- or p-vinyltoluene or a mixture thereof, including each of (a)–(f);

(k) the hydrolytically-stable, vinylically-unsaturated precursor compound is o-, m- or p-divinylbenzene or a mixture thereof, including each of (a)–(f);

(l) the hydrolytically-stable, vinylically-unsaturated precursor compound contains one or more of an oxygen atom, a nitrogen atom, a sulfur atom or a phosphorus atom or a combination thereof, including each of (a)–(f);

(m) the hydrolytically-stable, vinylically-unsaturated compound is acrylonitrile or methacrylonitrile, including each of (a)–(f);

(n) the hydrolytically-stable, vinylically-unsaturated precursor compound is an acrylate or methacrylate ester, wherein the alcohol moiety is alkyl of 1–30 carbon atoms or substituted or unsubstituted mono- or bicyclic aryl, including each of (a)–(f);

(o) the vinylically-unsaturated product compound is a reaction product of 4-bromobenzocyclobutene and m- or p-vinyltoluene, or a mixture thereof;

(p) the vinylically-unsaturated product compound is a reaction product of 4-bromobenzocyclobutene and divinylbenzene;

(q) the vinylically-unsaturated product compound is a reaction product of ethylene and o- or p-bromotoluene;

(r) the vinylically-unsaturated product compound is a reaction product of ethylene and 4-bromobenzocyclobutene;

(s) the vinylically-unsaturated product compound is a reaction product of styrene and 4-bromobenzocyclobutene;

(t) the catalyst is formed from palladium (II) acetate and a triaryl phosphine, including each of (a)–(s);

(u) the catalyst is formed from a palladium (O) complex and a triarylphosphine, including each of (a)–(s);

(v) the catalyst is formed from palladium (II) acetate and tris-(o-tolyl)phosphine, including each of (a)–(s);

(w) the inorganic hydrogen halide acceptor is an alkali metal hydroxide, carbonate, acetate or propionate, including each of (a)–(v);

(x) the inorganic hydrogen halide acceptor is potassium acetate, including each of (a)–(v);

(y) the inorganic hydrogen halide acceptor is sodium acetate, including each of (a)–(v);

(z) an optional organic hydrogen halide acceptor is a secondary or tertiary amine, including each of (a)–(y);

(aa) an optional organic hydrogen halide acceptor is represented by the formula $R_1R_2R_3N$ and each of $R_1$, $R_2$ and $R_3$ is selected independently from straight-chain and branched-chain alkyl of 1–8 carbon atoms and cycloalkyl, including each of (a)–(y);

(bb) the organic hydrogen halide acceptor is triethylamine, including each of (a)–(y);

(cc) the diluent is water, including each of (a)–(bb);

(dd) the diluent is water and is present in amount exceeding 100% by weight of combined halogenated organic compound and hydrolytically-stable, vinylically-unsaturated precursor compound, including each of (a)–(bb);

(ee) the diluent is an aqueous solution of up to 90% by volume of an organic solvent selected from the group consisting of nitriles, alcohols, linear or cyclic saturated esters, N,N-dialklformamides, N-alkylpyrrolidinones, alkoxyalkanols, glycol ethers, ketones, dioxane, tetrahydrofuran, tetrahydropyran or hexaalkylphosphoramides, including each of (a)–(bb);

(ff) the diluent is an aqueous solution of 10–90% by volume of N,N-dimethylformamide, including each of (a)–(bb);

(gg) the diluent is an aqueous solution of 30–70% by volume of N-methylpyrrolidinone, including each of (a)–(bb);

(hh) the diluent is an aqueous solution of 30–70% by volume of N,N-dimethylformamide or N-methylpyrrolidinone and the diluent is present in an amount equal to at least 70% by weight of combined halogenated organic compound, hydrolytically-stable, vinylically-unsaturated precursor compound and organic hydrogen halide acceptor, including each of (a)–(bb);

(ii) a further step of treating a resulting crude product with a peroxide is included, including each of (a)–(hh);

(jj) a further step of chromatographing a resulting crude product over silica or alumina is included, including each of (a)–(hh); and (kk) the further steps of treating a resulting crude product with a peroxide and chromatographing the crude product over silica or alumina are included, including each of (a)–(hh).

In the aspect of this invention, relating to the synthesis of vinylically-unsaturated organosilicon compounds, the preferred hydrolytically-stable precursor compounds are vinyl, allyl or methallyl organosilicon compounds, reacted with halides as above. Particularly preferred precursor compounds are:

(a) a vinyl, allyl or methallyl organosilicon compound, (b) a trialkylvinylsilane, wherein alkyl is of 1–6 carbon atoms, (c) a compound of the formula

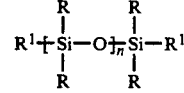

wherein each R is independently alkyl of 1–6 carbon atoms, cycloalkyl, aralkyl or phenyl; each $R^1$ is independently vinyl, allyl or methallyl and n is an integer from 1 to 4500, and (d) $[CH_2=CH-Si(CH_3)_2]_2O$.

Most preferred products are those prepared from 4-bromobenzocyclobutene and 1,1'-divinyltetramethyldisiloxane or an alpha,omega-divinyl(dimethylsiloxane) oligomer.

A most preferred organic peroxide for treatment of organophosphine residues is tert-butyl hydroperoxide.

BEST MODE FOR CARRYING OUT THE INVENTION

Most preferred products, prepared by the process of this invention are those prepared from:
(a) 4-bromobenzocyclobutene and a mixture of m- and p-vinyltoluene,
(b) 4-bromobenzocyclobutene and divinylbenzene (c) ethylene and o-bromotoluene
(d) ethylene and 4-bromobenzocyclobutane and
(d) styrene and 4-bromobenzocyclobutane.

A most preferred catalyst is that formed from palladium (II) acetate and tris(o-tolyl)phosphine.

A most preferred diluent is aqueous dimethylformamide, containing 30-70% by volume of N,N-dimethylformamide.

Most preferably, a resulting crude product is treated with aqueous hydrogen peroxide or with tert-butyl hydroperoxide.

SPECIFIC EMBODIMENTS

Without further elaboration it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the following examples, the temperatures are set forth uncorrected in degrees Celsius. Unless otherwise indicated, all parts and percentages are by weight.

EXAMPLE 1

Coupling of Bromobenzene with Ethyl Acrylate; Aqueous DMF; KOAc

To a 100-mL, one-necked flask, equipped with a polytetrafluoroethylenecoated magnetic stirring bar, reflux condenser and thermometer well, is charged 10.71 g (0.1092 mol) of potassium acetate and 12.5 mL of deionized water. After the potassium acetate has dissolved, 8.57 g (0.0546 mol) of bromobenzene, 5.46 g (0.546 mol) of ethyl acrylate, 0.0246 g (0.00011 mol) of palladium (II) acetate, 0.134 g (0.00044 mol) of tris-(o-tolyl)phosphine and 25 mL of N,N-dimethylformamide are added to the stirred mixture. The atmosphere over the reaction mixture is purged with nitrogen and a nitrogen pad is maintained over the mixture throughout the reaction. The mixture is stirred and heated at 90° C. for 16 hr. Gas chromatographic analysis of the mixture shows that the mixture contains 96.5% of ethyl 3-phenylpropenoate.

$^1$H NMR (CDCl$_3$): δ 7.6 (d, 1H, J=32 Hz); 6.4–7.4 (m, 5H), 6.3 (d, 1H, J=32 Hz), 4.2 (q, 2H, J=14 Hz), 1.3 (t, 3H, J=14 Hz).

EXAMPLE 2

Coupling of Bromotoluene with Ethylene

Reactions are run in a stainless steel 2-L Parr reactor, equipped with an air-motor-driven stirring shaft, gas inlet tube equipped for purging with nitrogen and ethylene, pressure gauge, sampling system, internal thermowell, frangible blow-out member and a vent. Heating is provided by an electrically-heated mantle, connected to a high-limit shutoff and a West temperature controller, attached to a Molytek model 2702 recorder.

Samples are analyzed by GC using a Hewlett-Packard 5890 gas chromatograph with a flame ionization detector, a 7676A automatic sampler and a Hewlett-Packard 3390 integrator using known standard of pure o- or p-vinyltoluene (OVT, PVT). The column is 15 m×0.32 mm DB-5 (0.1 micrometer film) fused silica capillary. The injector temperature is 250° C.; the detector temperature is 300° C. The program is: maintain at 70° C./2 min; heat at 8° C./min ramp to 230° C. The flow rate for carrier gas is 1.7 atm (gauge), mu=38 cm/sec (isobutane at 200° C.). Flow rates are: hydrogen, 30 mL/min; air 400 mL/min, make-up, 30 mL/min (helium), split flow, 187 mL/min (helium). The septum purge rate is 0.56 mL/min. The sample size (automated) is 2 microL.

(a) Coupling in Aqueous DMF; o-Bromotoluene; Triethylamine

To the reactor is charged 374 g (2.187 mol) of 2-bromotoluene (98%, Aldrich), 442 g of triethylamine (reagent grade, Fisher), 0.59 g (0.0026 mol) of palladium (II) acetate (Engelhard), 3.18 g (0.0104 mol) of tris-(o-tolyl)phosphine (Strem Chemical Co.), 600 mL of N,N-diemthylformamide (Fisher) and 300 mL of deionized water. The reactor is sealed and attached to the reaction system. After stirring is initiated, the contents of the vessel are purged with nitrogen (5.44 atm, gauge) five times. The nitrogen is vented and the reactor is charged with ethylene (Scott Gas) to 5.10 atm, gauge and held at this pressure.

A sample of about 5 mL is removed from the double-valved sample dip tube and used for a gas chromatography trace of the initial feed sample. Additional samples are removed during the reaction by discarding the first several samples to rinse the dip tube before using a later sample for GC analysis.

The temperature controller is set at 75° C. and heating is initiated. The contents of the reactor reached the selected temperature after 30 min and is maintained at that temperature for the duration of a run.

A mixture of pure o-vinyltoluene and o-bromotoluene is analyzed on the GC. o-Vinyltoluene and o-bromotoluene have retention times of 0.89 min and 1.14 min, respectively. The contents of the reactor are sampled after 2, 4, 20.5, 28 and 45 h. The conversion of o-bromotoluene is incomplete after 45 h. The reactor is cooled to 30° C. and opened in a hood for the addition of 0.030 g of palladium acetate and 1.59 g of tris-(o-tolyl)phosphine. The vessel is resealed, reattached to the system, purged with nitrogen as before and repressurized with 5.10 atm (gauge) of ethylene. The contents of the reactor are heated to 75° C. At the end of 2 hours' further heating, the sample removed shows complete conversion. The contents of reactor are stirred and cooled to room temperature. The reactor is vented and the reaction vessel is opened.

The contents of the reactor are poured into a 5-L three-necked glass round-bottom flask containing 1 L of methylene chloride (Burdick & Jackson) and 1 L of deionized water. The flask has a bottom dump valve and is stirred by an air-driven stirrer. The contents of the flask are stirred for 5 min and the top aqueous phase is discarded. The organic phase is washed with two 1.5-L portions of deionized water; two 250-mL portions of 5N HCl in 1250 mL of deionized water and two further 1.5-L portions of deionized water. The aqueous layer is discarded after each wash.

The organic phase is filtered through a short column prepared using a 300 mL Fisherbrand microfiltration system with a 5-micron membrane filter, containing 150 mL of silica gel (Fisher, chromatographic 644 grade, type 150A, 100–200 mesh), topped with a 1.90 cm layer of magnesium sulfate. Filtration accomplishes removal of residual solids and catalyst and dries the solution.

Methylene chloride is removed from the filtrate on a Buchi Rotavaporizer Model RE 120 at 40° C. at 15 mm Hg. The weight of crude reaction product is 227.6 g. The crude product is charged to a 500-mL round-bottom flask and attached to a 20.32-cm Bantamware column packed with glass helices, attached to a Bantamware one-piece distillation unit equipped with a vacuum-jacketed Vigreaux section and fraction cutter. The distillation setup is connected to a McCloud gauge, a nitrogen source, a dry ice (−78° C.) trap, high-vacuum pump, heating mantle, temperature controller and temperature high-limit cutoff. The crude product is degassed and methylene chloride is removed with stirring until bubbling stopped. The distillation pot is heated to 50° C. at about 0.4 mm Hg. The first fraction (about 20 g) is collected at 24°–25° C./0.35 mm Hg. The second fraction (114.7 g) is collected at a pot temperature up to 55° C. The first and second fractions are identified as 100% pure o-vinyltoluene (GC). The dry ice trap contains 31.6 g of o-vinyltoluene, containing a trace of methylene chloride. The pot residue (53.2 g) crystallizes upon cooling. The pot residue contains 3.5% of o-vinyltoluene (OVT), 60% of transdisubstituted product, 30% of 1,1 (gem)-disubstituted product and 4% of tris-(o-tolyl)phosphine.

The combined yield of OVT (134.7+31.6) is 166.3 g (64% of theory).

(b) Coupling in Aqueous DMF; Higher Catalyst Level; o-Bromotoluene; Triethylamine The reaction is as in (a), except that 0.98 g (0.00437 mol) of palladium (II) acetate and 5.32 g of tris-(o-tolyl)-phosphine are used as catalyst. The reactor is loaded as above and the temperature is increased to 120° C. Ethylene pressure is 13.6 atm, gauge. Samples are taken for analysis at 0, 3 and 5 h. At the end of 5 h, only a trace of bromotoluene is present (GC). The product contains 75.3% of OVT, 16% of trans-diadduct and 6.8% of gem-diadduct. The reactor is shut down after 7 hours' heating, as above.

The product is worked up as above to give 241 g of crude product. The mixture is purified by distillation at 8.0 mm Hg, at which product boiled at 50°–51° C. and no product was collected in the cold trap. The first cut gave 10 g of OVT (99%); the second cut gave 131 g of OVT (99.34%). A third cut (25.4 g 50°–51° C., 8 mm Hg) contains 98.6% of OVT and 1.2% of o-bromotoluene.

The pot residue (61.2 g) is mainly diadduct. The recovered OVT weights 166.4 g (64.4% of theory).

(c) Coupling of p-Bromotoluene and Ethylene; Aqueous DMF; Triethylamine

The reaction is run as in part (b), except that p-bromotoluene is used instead of o-bromotoluene. The reaction is run at 123° C., with cooling to 112° C. after an initial exotherm. Samples are taken at 0, 3 and 5 h and used for GC analyses. At the end of three h, the GC shows 77.65% of p-vinyltoluene (PVT), less than 0.5% of p-bromotoluene, 18.1% of trans-diadduct and 3.0% of gem-diadduct. The reactor is cooled after 5 hours' heating, at which point GC indicates complete conversion of bromotoluene to 73.5% PVT, 20.9% of trans-diadduct and 3.4% of gem-diadduct.

The product is worked up as in (b), except that 1.5 L of additional methylene chloride is used to dissolve precipitated solids. The solids are isolated, purified and characterized as trans-p-methylstibene dicoupled product, m.p. 179° C. (51 g). The total yield of isolated crude products is 225.5 g, comprising 72.9% of PVT, 22.0% of trans-diadduct, 3.2% of gem-diadduct and 1.2% of tris-(o-tolyl)phosphine.

(d) Coupling of p-Bromotoluene and Ethylene; Aqueous DMF; KOAc

The reaction is run as in (c), except that 429 g (4.37 mol) of KOAc is used, instead of triethylamine. At the end of three hours, the reaction mixture contains 88.9% of PVT, 4.5% of bromotoluene, 3.76% of trans-diadduct and 2.26% of gemdiadduct. Attempted sampling of the contents of the reactor fails after 5 h, because precipitated diadduct clogs the sample tube. The reaction is stopped after 7 h. The yield of isolated crude products is 225.3 g, comprising 82.8% of PVT, 3.86% of trans-diadduct, 8.4% of gem-diadduct and 3.21% of tris-(o-tolyl)phosphine.

EXAMPLE 3

Coupling of 4-Bromobenzocyclobutene with Vinyltoluene (a) Coupling in Aqueous DMF; NaHCO₃

To a 100-mL flask, equipped with a magnetic stirring bar, thermowell and condenser are charged 0.0122 g of palladium acetate, 0.0664 g of tris-(o-tolyl)phosphine, 10.0 g of bromobenzocyclobutene, 6.44 g of commercial grade m/p-vinyltoluene, 9.17 g of sodium hydrogen carbonate, 25 mL of N,N-dimethylformamide and 12.5 g of HPLC grade water. The system is purged with nitrogen and then heated to about 95° C. for 17 h. Some of the sodium hydrogen carbonate remained as a solid at the bottom of the reaction mixture. After 17 hours, a sample of the top organic layer was analyzed by GC. The sample contains no Br-BCB, a trace of vinyltoluenes and 1-(4-benzocyclobutenyl)-2-(m/p-tolyl)ethylene.

The contents of the flask are cooled and added to a mixture of 100 mL of deionized water and 25 mL of toluene. The organic phase is washed with four 100-mL portions of deionized water to remove sodium bromide and unreacted sodium hydrogen carbonate. After separating the organic layer, which is dried over magnesium sulfate, toluene in the organic layer is removed on a rotavaporator. The product is analyzed by GC/MS and has a parent peak of 220 mass units.

(b) Coupling in Aqueous DMF; 2-Picoline; KOH

The reaction is run as in (a), except that 10.17 g of 2-picoline is used as hydrogen halide acceptor. After 24 hours' heating at 95° C., only a trace of product is obtained (GC). Potassium hydroxide (1 equivalent) is added to the mixture, which is heated at 95° C. overnight. The resulting mixture contains less than 1% of bromobenzocyclobutene; the balance is 1-(4-benzocyclobutenyl)-2-(tolyl)ethylene.

(c) Aqueous DMF; NaOH; no Phosphine

To a 100-mL round-bottom flask, equipped with a stirring bar, reflux condenser and thermowell, is charged 10.0 g of bromobenzocyclobutene, 6.44 g. of commercial m/p-vinyltoluene, 2.19 g of sodium hydroxide, 0.0122 g of palladium acetate, 225 mL of N,N-dimethylformamide and 12.5 mL of water. The reaction mixture is heated at 95° C. for 20 h. A sample contains (GC) 30% of Br-BCB and 33% of 1-(4-benzocyclobutenyl)-2-(tolyl)ethylene. After adding 0.0122 g of palladium acetate, the mixture is heated at 95° C. for two days more. The yield of 1-(4-benzocyclobutenyl)-2-(tolyl)ethylene increases to 35% (GC).

EXAMPLE 4

(a) Coupling of 4-Bromobenzocyclobutene with 1,1'-Divinyltetramethyldisiloxane

To a 250 mL-round bottom flask, equipped with magnetic stirrer and reflux condenser, are charged 10.0 g of 4-bromobenzocyclobutene, 5.08 g of 1,1'-divinyltetramethyldisiloxane, 11.0 g of triethylamine, 0.0246 g of palladium (II) acetate, 0.134 g of tris-(o-tolyl)phosphine, 25 mL of deionized water and 50 mL of DMF. The reactor is purged with nitrogen for 30 min at room temperature and then heated under reflux for 20 h. GC analysis shows that all of the BrBCB is reacted.

At the end of 24 h under reflux, the reaction mixture contains 5.3% of 4-vinylbenzocyclobutene, 9.6% of 1-[(4-benzocyclobutenyl)vinyl]-1'-vinyltetramethyldisiloxane, 17.4% of 1,2-bis-(4-benzocyclobutenyl)ethylene and 48.1% of 1,1'-bis-[(4-benzocyclobutenyl)vinyl]tetramethyldisiloxane.

This experiment shows that increasing the amount of mixed solvent has little effect on the reaction.

(b) Low Catalyst Level; KOAc

An experiment is run as in (a), except that potassium acetate (16.08 g, 0.1638 mol) is used as hydrogen halide acceptor, the catalyst comprises 0.0123 g (0.00055 mol) of palladium acetate and 0.067 g (0.00022 mol) of tris-(o-tolyl)phosphine and the solvent comprises 25 mL of DMF and 12.5 mL of deionized water. The reaction mixture is heated at 95° C. for 16.5 h, at which point the mixture contains 0.8% of 4-vinylbenzocyclobutene, 3.0% of BrBCB, 3.1% of DVS-BCB, 6.5% of trans-1,2-bis-(4-benzocyclobutenyl)ethylene and 73.1% of 1,1'-bis-[(4-benzocyclobutenyl)vinyl]-tetramethyldisiloxane.

EXAMPLE 5

Coupling of 4-Bromobenzocyclobutene with 1,1'-Divinyltetramethyldisiloxane

To a 100-mL round bottom flask, equipped with magnetic stirring bar, thermowell and reflux condenser are charged 10.0 g of 4-bromobenzocyclobutene, 5.08 g of 1,1'-divinyltetramethyldisiloxane, 8.95 g of sodium acetate, 0.0246 g of palladium (II) acetate, 0.134 g of tris-(o-toly)phosphine, 25 mL of DMF and 12.5 mL of deionized water. The reaction mixture is purged with nitrogen for 30 min at room temperature and stirred and heated under reflux for 20 h. At the end of 20 h, GC analysis shows that 72% of the bromobenzocyclobutene (BrBCB) is unreacted. The reaction mixture also contains 1.0% of 4-vinylbenzocyclobutene (VBCB), 18.7% of 1-[(4-benzocyclobutenyl)vinyl]-1'-vinyltetramethyldisiloxane (DVS-BCB), and 4.1% of 1,1'-bis-[(4-benzocyclobutenyl)vinyl]tetramethyldisiloxane (DVS-BCB$_2$).

At the end of 24 h, the reaction mixture contains 61.3% of BrBCB, 2.9% of VBCB, 22% of DVS-BCB and 10.7% of DVS-BCB$_2$. At the end of 42 hr, the contents of the reaction mixture are 4.8% BCB, about 4% DVS-BCB, 10.3% of 1,2-bis-(4-benzocyclobutenyl)ethylene and 68.2% DVS-BCB$_2$.

This run corresponds to Run B:1 in Table 2.

Results of other experiments, on a laboratory scale, are shown in Table 2.

TABLE 2

Synthesis of Divinyltetramethyldisiloxane-bis(benzocyclobutene) Adduct

| Run | Moles Base/BrBCB | | | Time (h) | Solvent[a] | Scale | Yield (%) (DVS—BCB$_2$) |
|---|---|---|---|---|---|---|---|
| | Et$_3$N | KOAc | NaOAc | | | | |
| A:1 | 2 | — | — | 29 | DMF/H$_2$O | 100 mL | 45.2 |
| A:2 | 2 | — | — | 26 | DMF/H$_2$O | 22 L | 47.6 |
| B:1 | — | — | 2 | 42 | DMF/H$_2$O | 100 mL | 68.2 |
| B:2 | — | — | 2 | | DMF | 100 mL | trace |
| B:3 | — | — | 2 | | water | 100 mL | 3.5 |
| B:4 | — | — | 1 | 44 | DMF/H$_2$O | 100 mL | 38.0 |
| B:5 | — | — | 2 | | " | 5 L | 60.4 |
| B:6 | — | — | 1.5 | 23 | " | 100 mL | 65.6 |
| B:7 | 1 | — | 2 | 23 | " | 100 mL | 77.9[c] |
| B:8 | 1 | — | 1 | | " | 100 mL | 72.6 |
| B:9 | 2 | — | 2 | | " | 100 mL | 76.5 |
| B:10 | 1 | — | 2 | | " | 100 mL | 70.9 |
| B:11 | 1 | — | 1.5 | 20 | " | 100 mL | 76.5 |
| B:12 | 1 | — | 1.5 | | DMF/H$_2$O | 5 L | 82.3 |
| B:13 | 1 | — | 2 | | NMP/H$_2$O[b] | 100 mL | 49.2 |
| C:1 | 1 | 2 | — | 23 | DMF/H$_2$O | 100 mL | 79.4[d] |
| C:2 | 1 | 1.5 | — | 27 | " | 22 L | 82.0 |
| C:3 | 1 | 1.5 | — | 43 | DMF/H$_2$O−15% | 22 L | 75.9 |
| C:4 | 1 | 1.5 | — | 27 | DMF/H$_2$O+10% | 22 L | 69.5 |
| C:5 | 1 | 1.5 | — | 26 | DMF/H$_2$O | 22 L | 74.2 |
| C:6 | 1 | 1.5 | — | 24 | " | 22 L | 77.3 |
| C:7 | 1 | 1.5 | — | 25 | " | 22 L | 82.8 |
| C:8 | 1 | 1.5 | — | 26 | " | 22 L | 77.2 |
| C:9 | 1 | 1.5 | — | 24 | " | 22 L | 77.9 |
| C:10 | 1 | 1.5 | — | 20 | " | 22 L | 79.8 |

(a) 2:1 DMF:H$_2$O v/v, unless otherwise indicated
(b) N-Methylpyrrolidone:water 2:1 v/v
(c) No BCB, 7.4% BCB—C=C—BCB, 77.9% DVS—BCB$_2$ and 1% heavier
(d) No BCB, 2.3% DVS—BCB, 3.1% DVS—BCB—OH, 4.7% BCB—C=C—BCB, 79.4% DVS—BCB and 1.2% heavier

EXAMPLE 6

Scaled-up Coupling of 4-Bromobenzocyclobutene and 1,1'-Divinyltetramethyldisiloxane A 22-L reactor is prepared for the reaction by turning on nitrogen, introduced through a bubbler; turning on water for a reflux condenser; checking that dump valves at the bottom of the reactor are closed; charging reagents to the reactor; turning on the agitator. Nitrogen is passed through the liquid charge for 30 min. The heating cycle is initiated at this point and the temperature is checked after 45 min-1 h.

A typical reactor charge is:

| | |
|---|---|
| 3200 g | 4-BrBCB (2177 mL, Dow) |
| 1626 g | 1,1'-divinyltetramethyldisiloxane (Dow Corning XI-2297 fluid) |
| 1755 g | triethylamine (Fisher Scientific, Reagent Grade, 99%) |
| 43 g | tris-(o-tolyl)phosphine (Strem Chemical Co.) |
| 8 g | palladium (II) acetate (Engelhard, 47.4% Pd) |
| 2557 g | potassium acetate (Fisher Scientific, certified ACS) |

| | -continued |
|---|---|
| 4800 mL | DMF (4000 mL to reactor; 800 mL to rinse in catalyst mixture, Fisher Scientific, ACS) |
| 2400 mL | deionized water |

The reactor temperature is controlled to about 94°–97° C. for the duration of heating under reflux. At the end of 24 h, the reaction mixture is checked by GC for unreacted BrBCB, using a capillary GC 5890 apparatus. The column used (from J & W Scientific Co., Anspec, Ann Arbor, Mich. 48107), comprises a 15 meter wide bore capillary column, bonded with DB-5, having a film thickness of 1 micrometer. A flame ionization detector (HP 5890), integrator (HP 3392A) and autosampler (HP 7671A) are used. The retention time for BrBCB is 1.65 min, for DVS-BCB monoadduct 8–10.5 min, for trans-1,2-bis-(benzocyclobutenyl)ethylene about 16 min and for DVS-BCB$_2$ about 18.9–20.3 min.

If the BrBCB content is above about 2%, the reaction is continued and samples are taken every few hours and conversion of BrBCB is rechecked. If more than 2% of BrBCB is unreacted after 48 h, an additional charge of catalyst is employed.

When 98% of the BrBCB is reacted, heating for the reactor is shut off and the contents of the reactor are allowed to cool to 70° C. over about 1.5 h. Part of the water (ca 9.5 L) is removed through a bottom dump. To the reactor is added 3 L of heptane and 10 L of deionized water and the contents of the reactor are stirred for 15 min and allowed to settle. Part of the water layer is removed through a bottom dump.

An additional 10 L of deionized water is added and the contents of the reactor are stirred for 15 min and allowed to settle. Part of the water layer is removed, as above.

To the reactor are added 10 L of deionized water and 500 mL of 5N hydrochloric acid. The resulting mixture is stirred for 15 min and allowed to settle. Part of the water layer is removed, as above.

Deionized water (10 L) is added and the mixture is stirred for 15 min and allowed to settle. The pH of the mixture is checked. Part of the water is removed.

Another portion of deionized water (10 L) is added. The mixture is stirred for 10 min and allowed to settle. The pH is checked. Part of the water layer is removed. If pH is more acidic than 6–7, the contents of the reactor are washed with further portions of water. Otherwise the upper product layer is removed.

The product layer is filtered using a Fisherbrand 1-L membrane filter assembly with a 5-micron nylon filter, covered with 90 g of silica (Davison Chemical, Chromatographic Grade 62, 60×200 mesh) and 0.635 cm of magnesium sulfate, covered with glass wool. The crude filtrate is collected and chromatographed on a column (6.35 cm inner diameter, 106.68 cm in length), filled with 1200 g of silica in heptane. The excess heptane is removed from the column, which is not permitted to run dry. The effluent from the column is evaporated, using a rotary evaporator. The yield of DVS-BCB$_2$ can be determined at this point, using a Hewlett-Packard 5890 gas chromatograph with a Hewlett-Packard 7671A autosampler and H-P 3392A integrator, using a J & W 15-meter wide-bore capillary column bonded with DB-5, 0.10 micrometer film thickness. The temperature program is: isothermal at 50° C. or 70° C. for 2 min, ramp at 8° C. to 230° C., hold at 230° C. for 8 or more min.

The residual product is treated with aqueous hydrogen peroxide, as above.

Chromatography on silica gel can be repeated and the heptane eluant can be removed, using a rotary evaporator.

The products are analyzed at this point by GC analysis for DVS-BCB$_2$, by neutron activation analysis for Cl, Br, P, Na, K and Pd and by LC analysis for higher molecular weight components.

Yields for representative runs are given in Table 2.

EXAMPLE 7

Reaction of Bromobenzocyclobutene with Olefins; Aqueous DMF; LiOAc (a) Reaction with Divinyltetramethyldisiloxane To a 100-mL one-necked flask, equipped with a polytetrafluoroethylene-coated magnetic stirrer, reflux condenser and thermometer well, is charged 12.5 mL of deionized water and 11.16 g (0.1092 mol) of lithium acetate. The mixture is stirred to dissolve the lithium acetate, after which 10.0 g (0.0546 mol) of bromobenzocyclobutene, 5.08 g (0.0273 mol) of divinyltetramethyldisiloxane (DVS), 0.0246 g (0.00011 mol) of palladium acetate, 0.134 g (0.00022 mol) of tris-(o-tolyl)phosphine and 25 mL of N,N-dimethylformamide are charged to the flask. The atmosphere in the flask is replaced with nitrogen and an atmosphere of nitrogen is maintained throughout the reaction.

The mixture is stirred and heated at 93° C. for 45.5 h. The crude reaction mixture contains no bromobenzocyclobutene, 15% of vinylbenzocyclobutene, 1.6% of gem-DVS-BCB, 2.1% of trans-DVS-BCB, 9.6% of bis-(4-benzocyclobutenyl)ethylene, 51.5% of DVS-bis-BCB and 7.5% of higher condensates.

(b) Reaction with Styrene

The reaction is carried out as in (a), using 5.68 g (0.0546 mol) of styrene instead of DVS.

After heating at 93° C. for 45.5 h, the reaction mixture contains no bromobenzocyclobutene and 84.0% of styrylbenzocyclobutene (GC).

EXAMPLE 8

Condensation of Bromobenzocyclobutene with 1,1'-Bis-[(4-(benzocyclobutenyl)vinyl]tetramethyldisiloxane; Aqueous DMF; KOAc To a 100-mL, three-necked flask, equipped with a polytetrafluoroethylene-coated magnetic stirring bar, reflux condenser and thermometer well, is charged 7.5 mL of deionized water and 3.76 g (0.0843 mol) of sodium acetate. The mixture is stirred to dissolve the potassium acetate, after which 0.0256 g (0.00011 mol) of palladium acetate, 0.134 g (0.00044 mol) of tris-(o-tolyl)-phosphine, 2.34 g (0.0128 mol) of bromobenzocyclobutene, 5.00 g (0.0128 mol) of 1,1'-bis-[(4-benzocyclobutenyl)vinyl]tetramethyldisiloxane and 15 mL of N,N-dimethylformamide are added to the stirred mixture. The resulting mixture is purged with a stream of nitrogen for 30 min, after which the stirred mixture is heated to 90° C. and maintained at that temperature for 39 h.

At the end of this time, all of the bromobenzocyclobutene had reacted (GC). Toluene (25 mL) is added to the reaction mixture. The aqueous layer is separated and discarded. The organic layer is washed with 25-mL portions of deionized water and dried over magnesium sulfate. Removal of toluene under reduced pressure gives 4.3 g of crude product. GC analysis of the product indicates that one major product has formed. Direct exposure probe mass spectrometry demonstrates the presence of the tris-(4-benzocyclobutenyl) adduct in the product.

EXAMPLE 9 trans-Styrylbenzocyclobutene from Styrene and BrBCB

To a 5-L round-bottom flask, equipped with a heating mantle, bottom dump valve, thermowell, reflux condenser and stirrer assembly, is charged 0.98 g of palladium acetate, 5.327 g of tris-(o-tolyl)phosphine, 800 g of 4-BrBCB, 1072.78 g of potassium acetate, 1000 mL of N,N-dimethylformamide, 500 mL of deionized water and 454.40 g of freshly-distilled styrene. The reactor is degassed with nitrogen, heated to about 93° C. and maintained at that temperature for 27 h. The crude reaction product contains 0.85% of BrBCB and 96.74% of styrylbenzocyclobutene.

The reaction mixture is cooled to 70° C. and 1 L of hot deionized water and 1 L of toluene are added. The resulting water layer is separated and discarded. The organic layer is washed with three further 1.5-L portions of deionized water. The organic phase is cooled to room temperature and diluted with 500 mL of toluene. The resulting organic phase is filtered through 150 g of silica gel, topped with 40 g of magnesium sulfate, on a 1.0 micrometer membrane filter. Toluene is removed from the filtrate on a rotavap to leave 975.45 g of crude product. This is recrystallized from 2 L of hot ethyl acetate. The crystallized product is filtered, washed with ethanol and dried overnight at 50° C. The first crop weigh 260 g, the second 378 g and the third 71.2 g. The product corresponds to a fully-characterized standard.

EXAMPLE 10

Coupling of Bromobenzocyclobutene and Divinyltetramethyldisiloxane; Aqueous DMF; Triethylamine and KOAc To a 5-L, round-bottom flask, equipped with heating mantle, bottom dump valve, thermowell, reflux condenser and stirrer assembly, is charged 0.72 g of palladium acetate, 3.87 g of tris-(o-tolyl)phosphine, 290.9 g (1.59 mol) of 4-BrBCB, 591.5 g (3.18 mol) of divinyltetramethyldisiloxane, 160.5 g of triethylamine, 234 g of potassium acetate, 436 mL of N,N-dimethylformamide and 219 mL of deionized water. The reactor is degassed with nitrogen and the contents heated to about 100° C. and held at that temperature for two days. The crude reaction product contains no BrBCB (GC), 70.55% of 1-[(4-benzocyclobutenyl)vinyl]-1'-vinyltetramethyldisiloxane (BCB-DVS) and 14.69% of 1,1'-bis-[(4-benzocyclobutenyl)vinyl]tetramethyldisiloxane (DVS-BCB$_2$).

The reactor is cooled to 80° C. and the contents are diluted with 2000 mL of water and 500 mL of heptane. The water layer is separated and discarded. The organic layer is washed with three 2-L portions of deionized water. The organic phase is filtered through 150 g of silica, topped with about 40 g of magnesium sulfate, on a 5-micrometer membrane filter. Heptane is removed from the filtrate on a rotavap to give 398 g of amber liquid.

The crude is distilled overhead on a short path molecular distillation unit at 1-2 microns Hg at 80° C. to give 261.46 g (57% isolated yield) of trans-DVS-BCB (95.47% purity). The bottoms cut (118 g) contains DVS-BCB, which can be redistilled.

EXAMPLE 11

Reaction of 4-Acetoxystyrene with 4-Bromobenzocyclobutene; Aqueous DMF; KOAc To a 5-L round-bottom flask, equipped with heating mantle, bottom dump valve, thermowell, reflux condenser and stirrer assembly, is charged 0.604 g of palladium acetate, 3.374 g of tris-(o-tolyl)phosphine, 480.91 g of 4-BrBCB, 515.31 g of potassium acetate in 575 mL of deionized water, 1150 mL of N,N-dimethylformamide and 341.3 g of 4-acetoxystyrene.

The reactor is degassed with nitrogen and heated to about 90° C. and held at about 90° C. for 15.5 h. The crude reaction product (GC) contains 13% of 4-BrBCB, 37% of [(4-benzocyclobutenyl)vinyl]phenol and 33% of [(4-benzocyclobutenyl)vinyl]phenyl acetate. A sample, taken after 19.5 hours' heating contains 9.6% of 4-BrBCB, 44% of [4-benzocyclobutenyl)vinyl]phenol and 25% of [(4-benzocyclobutenyl)vinyl]phenyl acetate.

The crude product is treated with caustic to form a water-soluble sodium phenate, which is acidified and separated to yield 350 g of high purity [(4-cyclobutenyl)vinyl]phenol (97% by GC area).

EXAMPLE 12

Ethyl beta-trans-(4-Benzocyclobutenyl)acrylate; Aqueous DMF; KOAc

To a 5-L three-necked flask, equipped with an air-driven stirrer, condenser and thermocouple well, is charged 2.02 g of palladium acetate, 10.96 g of tris-(o-tolyl)phosphine, 502.3 g of 4-bromobenzocyclobutene, 276 g of ethyl acrylate, 542 g of potassium acetate, 823 mL of N,N-dimethylformamide and 411 mL of deionized water. The reactor is purged with nitrogen and a nitrogen atmosphere is maintained over the reactor. The reaction mixture is stirred and heated to 93° C. for 16 h. A sample of the product at this point contains no BrBCB and 84.8% of trans-BCB—CH=CHCOOC$_2$H$_5$.

The reactor is cooled and 1 L of deionized water is added. The water layer is separated and discarded. The mixture is diluted with 1 L of toluene and the organic phase is washed with five 1-L portions of deionized water. The organic phase is filtered through 150 mL of silica gel, topped by 40 g of magnesium sulfate, on a membrane filter. Solvent is evaporated from the filtrate to give 521 g of crude product.

The proton NMR spectrum of the crude product is compared to that of ethyl cinnamate. Part of the crude product is purified by vacuum distillation at 103° C./0.24 mm Hg to purity above 98% (GC). This material has a parent ion at m/e=202 by GC/MS.

EXAMPLE 13

Reaction of Bromobenzocyclobutene with Divinyl(dimethylsiloxane) Oligomers (a) To a 1-L round-bottom flask, fitted out with a magnetic stirrer, heating mantle, reflux condenser and temperature controller, is charged 94 g of 4-bromobenzocyclobutene (0.51 mol), 150 g of alpha,omega-divinyl(dimethylsiloxane) oligomers (Petrarch Systems, average mol. wt. 720, 0.20 mol), 58.6 g of triethylamine (0.58 mol), 42.2 g of potassium acetate (0.43 mol), 0.194 g of palladium acetate (0.864 mmol), 1.053 g of tris-(o- tolyl)phosphine (3.46 mmol), 250 mL of N,N-dimethylformamide and 125 mL of deionized water.

The contents of the flask are purged with nitrogen for 30 min and then heated to 92° C. for 22 h. Additional 4-bromobenzocyclobutene (7.5 g) is added and heating is continued. At the end of 44 h, 7.5 g of additional 4-bromobenzocyclobutene and 15.0 g of triethylamine are added to the reaction mixture. Heating is continued for a total of 68 h.

The crude reaction mixture is poured into a 2-L separatory funnel, containing 1 L of deionized water. The bottom phase is removed and toluene (200 mL) is added to the organic layer. The organic layer is washed with four 1-L aliquots of deionized water, with 50 mL of 1N HCl in 950 mL of deionized water and with four 1-L aliquots of deionized water. The organic layer is filtered through a membrane filter, packed with silica gel layer (2.54 cm) and a magnesium sulfate layer (2.54 cm). The filtrate is concentrated by a rotary evaporator at 65° C. to remove most of the solvent and at 100° C. under high vacuum for 2 h. The weight of recovered product is 199.6 g.

After two days' standing at room temperature trans-1,2-bis-(4-benzocyclobutenyl)ethylene precipitates and is recovered by filtration (5 g). The mother liquors are passed through a column of silica gel (4.445 cm id×34.925 cm high), using heptane as eluant. Solvent was removed from the eluate using a rotary evaporator. The residue weighs 147 g.

The residue is charged to a 1-L round-bottom flask fitted out with a magnetic stirring bar. Heptane (150 mL) and methanol (75 mL) are charged to the flask. The mixture is stirred during the addition of 50-mL of 30% hydrogen peroxide in 10-mL portions over 30 min. The mixture is stirred at room temperature overnight. The mixture is washed with four 1-L aliquots of deionized water and dried over magnesium sulfate. The solution is passed through a column (4.445 cm id×46.99 cm high), packed with silica gel. The product is washed from the column with heptane. The solvent is removed using a rotary evaporator. The residue, weighing 136.7 g, is devolatilized with a wiped-film still at 100° C./70 microns Hg. The recovered bottoms fraction is devolatilized at 110° C./21 microns Hg. The product weighs 108.5 g and contains only traces of 4-bromobenzocyclobutene (GC).

(b) The same reaction is performed, using a mixture of vinyl-terminated dimethylsiloxane oligomers (mol wt 400–700, 4–10 dimethylsiloxane units). The product is recovered as above. The infrared spectrum of the bis-[(4-benzocyclobutenyl]vinyl)dimethylsiloxane oligomers is:

| Frequency | Assignment |
| --- | --- |
| 2975 cm$^{-1}$ | C—H stretch, methyl, dimethylsiloxane |
| 2840 | C—H stretch, methylene, benzocyclobutene |
| 1615 | quadrant stretching mode, benzocyclobutene |
| 1585 | quadrant stretching mode, benzocyclobutene |
| 1480 | ring stretching mode, benzocyclobutene |
| 1265 | C—H symmetric deformation, Si-methyl |
| 1205 | benzocyclobutene ring stretch (C—H out of plane deformation) |
| 1030 | Si—O—Si stretch |
| 995 | trans-olefin C—H out-of-plane stretch |
| 850 | Si-methyl rocking mode |
| 805 | Si-methyl rocking mode |

EXAMPLE 14

Reaction of 4-Bromobenzocyclobutene with Divinyltetramethyldisiloxane; KOAc; Anhydrous DMF To a 100-mL one-necked flask, equipped with a stirrer, condenser and thermometer well, are charged 16.08 g (0.1638 mol) of potassium acetate, 0.0123 g (0.000055 mol) of palladium acetate, 0.067 g (0.00022 mol) of tris-(o-tolyl)phosphine, 10.00 g (0.0546 mol) of 4-bromobenzocyclobutene, 5.08 g (0.0273 mol) of divinyltetramethyldisiloxane and 37.5 mL of DMF. The resulting solution is purged with a nitrogen stream for 70 min, after which the mixture is heated to 94° C. After 17.75 hours' heating the mixture contains 3.3% of 4-BrBCB and 65.9% of DVS-BCB$_2$(GC). The reaction is complete after 21.5 h, at which point no 4-BrBCB is detected by GC.

EXAMPLE 15

Similar experiments are run as follows:

| Olefin | Halide | Base | Solvent |
| --- | --- | --- | --- |
| VT | 4-IBCB | KOAc | DMF/water 2:1 |
| VT | 4-BrBCB | KOAc | DMF/water 1:2 |
| ST | 4-BrBCB | KOAc | MePy/water |
| VT | C$_6$H$_5$I | KOAc | NMP/water 2:1 |
| MA | C$_6$H$_5$CH$_2$Cl | NaOAc | DMF/water 2:1 |
| MA | C$_6$H$_5$CH$_2$Cl | KOAc | DMF/water 2:1 |
| AN | 4-BrBCB | LiOAc | DMF/water 1:1 |

AN = acrylonitrile,
ST = styrene,
VT = vinyltoluene
MA = methyl acrylate

Similar results are obtained.

EXAMPLE 16

(a) trans-1,2-Bis-(4-benzocyclobutenyl)ethylene

An experiment is run as in Example 3, using 0.28 g of palladium acetate, 1.50 g of tris-(o-tolyl)phosphine, 150 g of 4-bromobenzocyclobutene, 350 mL of N,N-dimethylformamide, 175 mL of deionized water and KOAc as hydrogen halide acceptor.

Product recrystallized from 100 mL of ethyl acetate is identified as trans-1,2-bis-(4-benzocyclobutenyl)ethylene, m.p. 132° C. GC analysis detects one peak (99.7 area %).

(b) 1,1,2-Tris-(4-benzocyclobutenyl)ethylene

To a 100-mL one-necked flask equipped with a polytetrafluoroethylene-coated magnetic stirring bar and thermometer well are charged 12.5 mL of deionized water, 5.57 g (0.0568 mol) of potassium acetate, 0.012 g (0.000026 mol) of palladium (II) acetate, 0.062 g (0.000103 mol) of tris-(o-tolyl)phosphine, 6.00 g (0.0258 mol) of trans-1,2-bis-(4-benzocyclobutenyl)ethylene and 25 mL of N,N-dimethylformamide.

The reaction is run as in the foregoing examples to give 1,1,2-tris-(4-benzocyclobutenyl)ethylene, m.p. 87°–89° C.

$^1$H NMR (CDCl$_3$): δ 6.6–7.3 (m, 10H), 2.9–3.3 (d, 12H); $^{13}$C[$^1$H] NMR (CD$_2$Cl$_2$, 75.1 MHz) 146.74, 146.31, 145.97, 145.82, 145.56, 145.09, 144.16, 144.00, 140.47, 137.33, 129.59, 129.50, 128.76, 127.22, 124.98, 123,81, 123.21, 122.67 122.62, 122.39, 29.80, 29.59.

EXAMPLE 17

(a) Experiments are run as in Example 3, using triphenylphosphine instead of tris-(o-tolyl)phosphine. Similar results are obtained. The catalytic species is believed to be bis(triphenylphosphine)palladium (0).

(b) Similar results are obtained, using tributylphosphine as a catalyst component.

(c) Similar results are obtained using as a catalyst component tris(dibenzylideneacetone)dipalladium (0) with triphenylphosphine or dichloro(triphenylphosphine)palladium (II).

EXAMPLE 18

(a) Coupling of 4-Bromobenzocyclobutene with Divinyltetramethyldisiloxane

The following reagents are used:

| | |
|---|---|
| 726 g | 4-bromobenzocyclobutene (3.97 mol) |
| 369 g | divinyltetramethyldisiloxane (1.98 mol) |
| 1134 g | potassium acetate (11.56 mol) |
| 0.90 g | palladium acetate |
| 4.88 g | tris-(o-tolyl)phosphine |
| 1090 mL | N,N-dimethylformamide |
| 545 mL | deionized water |

Water is charged to the reactor and stirred. Potassium acetate is charged to the reactor and stirred until dissolved. N,N-Dimethylformamide is charged to the reactor, followed by bromobenzocyclobutene, divinyltetramethyldisiloxane, palladium acetate and tris-(o-tolyl)phosphine. The resulting mixture is purged with a stream of nitrogen for 30 min. The reaction mixture is heated to 93° C. for 25 h, at which time GC indicates that the reaction is complete.

The reaction mixture is diluted with 1000 mL of deionized water. The contents of the reactor are cooled to 60° and stirring is stopped. After phase separation has occurred, the water layer is removed and discarded.

The organic layer is diluted with 750 mL of Isopar G. The organic phase is washed with 2500-mL portions of deionized water until the aqueous wash is neutral.

(b) Removal of Phosphine Residues from Product

The organic phase from (a) is stirred during the addition of 2.9 g (0.032 mol) of tert-butyl hydroperoxide. The mixture is stirred at 60° C. for 16 h and then cooled to room temperature. A filter is prepared by packing a column of suitable size with 400 g of silica gel and 90 g of magnesium sulfate, on top of a 5 micron filter. The organic solution is passed through the column and the column is washed with 500 mL of Isopar G. The eluate from the column is further processed as in Example 6.

Inorganic impurity content at various points of the purification procedure are:

| ppm | crude | filtered | distilled |
|---|---|---|---|
| Br | 159 | 10 | 1.9 |
| Cl | 3 | 7 | 3.3 |
| P | 305 | <2 | <0.3 |
| K | | <0.3 | |
| Na | | <0.2 | |
| Si | 8.6 | 6.3 | |

These results show that treatment of the crude product with an organic hydroperoxide produces a product, sufficiently pure for use in electronic applications.

EXAMPLE 19

Evaluation of Organic Oxidizing Agents for Reaction with Phosphines (a) Reaction with Butylene Oxide To a 100-mL round-bottom flask, fitted out with a magnetic stirring bar and condenser, is charged 100 g of hexane, 0.5 g (0.00164 mol) of tris-(o-tolyl)phosphine and 0.236 g (0.00328 mol) of butylene oxide. This mixture contains 99.2% of tris-(o-tolyl)phosphine and 0.37% of tris-(o-tolyl)phosphine oxide (GC analysis).

The mixture is heated at 60° C. for 82 h. The mixture contains 98.2% of tris-(o-tolyl)phosphine and 0.53% of tris-(o-tolyl)phosphine oxide.

(b) Reaction with Pyridine N-Oxide

To a 100-mL round-bottom flask, fitted out with a magnetic stirring bar and condenser, is charged 100 g of Isopar g, 0.5 g (0.00164 mol) of tris-(o-tolyl)phosphine and 0.16 g (0.00164 mol) of pyridine N-oxide. The reaction mixture contains 35.9% of tris-(o-tolyl)phosphine and 0.34% of tris-(o-tolyl)phosphine oxide (GC analysis).

The mixture is stirred and heated at 120° C. for 64 h. The reaction mixture contains 31.9% of tris-(o-tolyl)-phosphine and 1.57% of tris-(o-tolyl)phosphine oxide.

(c) Reaction with m-Chloroperoxybenzoic Acid

To a 100-mL round-bottom flask, fitted out with a magnetic stirring bar and reflux condenser, is charged 100 g of methylene chloride, 0.5 g (0.00164 mol) of tris-(o-tolyl)phosphine and 0.28 g (0.00164 mol) of m-chloroperoxybenzoic acid. The reaction mixture contains 37.4% of tris-(o-tolyl)phosphine oxide and no tris-(o-tolyl)phosphine (GC analysis). The mixture is passed through a column packed with 5 g of silica gel. GC analysis of the eluate shows that all of the tris-(o-tolyl)-phosphine oxide has been removed. The eluate is passed through a column packed with 5 g of basic alumina. GC analysis of the eluate shows that all of the m-chloroperbenzoic acid has been removed.

These experiments show that some oxidizing agents effectively convert a phosphine to a phosphine oxide. These experiments further show that a phosphine oxide can be adsorbed on silica gel and that a peroxidic oxidizing agent can be adsorbed on alumina.

EXAMPLE 20

Coupling of Ethylene and o-Bromotoluene; DMF

Experiments are run, as in Example 2, in a 10-gallon reactor. Build up of a salt cake on the stirrer impedes stirring. The salt cake must be removed after each run. Sampling of the reactor is complicated by accumulation of salts in the sampling tube.

From the foregoing description, one skilled in the art can easily ascertain the essential characteristics of this invention and, without departing from the spirit and scope thereof, can make various changes and modification of the invention to adapt it to various usages and conditions.

It is claimed:

1. A process for the preparation of a vinylically-unsaturated product compound, comprising reacting a halogenated organic compound with a hydrolytically-stable, vinylically-unsaturated precursor compound selected from the group consisting of (i) hydrocarbons and (ii) compounds containing one or more of an oxygen atom, a nitrogen atom, a phosphorus atom or a sulfur atom or a combination thereof, in the presence of (a) a homogeneous zerovalent palladium catalyst complex, (b) an inorganic hydrogen halide acceptor and (c) a diluent, wherein the diluent is water or an aqueous solution containing up to 95% by volume of an organic solvent, provided that at least some diluent water is in a second phase.

2. The process of claim 1, wherein the catalyst complex is formed from a palladium salt and an organophosphine or organoarsine.

3. The process of claim 1, wherein the catalyst complex is formed from palladium (II) acetate and tris-(o-tolyl)phosphine.

4. The process of claim 1, wherein the catalyst complex is formed from a palladium (0) complex and a triarylphosphine.

5. The process of claim 1, wherein the inorganic hydrogen halide acceptor is an alkali metal acetate, propionate, carbonate or hydroxide.

6. The process of claim 1, wherein the inorganic hydrogen halide acceptor is sodium acetate.

7. The process of claim 1, wherein the inorganic hydrogen halide acceptor is potassium acetate.

8. The process of claim 1, further including an organic hydrogen halide acceptor selected from a secondary or tertiary amine.

9. The process of claim 8, wherein the organic hydrogen halide acceptor is represented by the formula $R_1R_2R_3N$ and each of $R_1$, $R_2$ and $R_3$ is selected independently from straight-chain and branched-chain alkyl of 1-8 carbon atoms and cycloalkyl.

10. The process of claim 8, wherein the organic hydrogen halide acceptor is triethylamine.

11. The process of claim 1, wherein the diluent is water.

12. The process of claim 1, wherein the diluent is water and is present in amount exceeding 100% by weight of combined halogenated organic compound and hydrolytically-stable, vinylically-unsaturated precursor compound.

13. The process of claim 1, wherein the diluent is an aqueous solution consisting of up to 90% by volume of an organic solvent selected from the group consisting of nitriles, alcohols, linear or cyclic saturated esters, N,N-dialkylformamides, N-alkylpyrrolidinones, alkoxyalkanols, glycol ethers, dioxane, tetrahydrofuran, tetrahydropyran or hexaalkylphosphoramides.

14. The process of claim 1, wherein the diluent is an aqueous solution of 10-90% by volume of dimethylformamide or N-methylpyrrolidinone.

15. The process of claim 1, wherein the diluent is an aqueous solution of 30-70% by volume of dimethylformamide or N-methylpyrrolidinone.

16. The process of claim 1, wherein the diluent is an aqueous solution of 30-70% by volume of dimethylformamide or N-methylpyrrolidinone and the diluent is present in an amount equal to at least 70% by weight of combined halogenated organic compound and hydrolytically-stable, vinylically-unsaturated precursor compound.

17. The process of claim 1, wherein the halogenated organic compound is a bromo or iodo mono- or polycyclic substituted or unsubstituted carbocyclic or heterocyclic aromatic compound or a substituted or unsubstituted benzyl chloride, bromide or iodide.

18. The process of claim 1, wherein the halogenated organic compound is a brominated benzocyclobutene represented by the formula

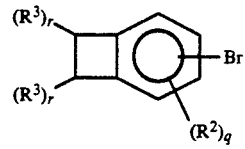

wherein $R^2$ is alkyl of 1-6 carbon atoms, alkoxy of 1-6 carbon atoms, trifluoroacetoxy, acyloxy of 1-6 carbon atoms, nitro or chloro; each $R^3$ is alkyl of 1-6 carbon atoms, aryl, nitro, chloro or cyano; q is 0, 1, 2 or 3 and each r is independently 0 or 1.

19. The process of claim 1, wherein the halogenated organic compound is 4-bromobenzocyclobutene.

20. The process of claim 1, wherein the halogenated organic compound is of the formula ArBr, wherein Ar is phenyl or o-, m- or p-tolyl.

21. The process of claim 1, wherein the halogenated organic compound is a substituted or unsubstituted benzyl chloride or bromide.

22. The process of claim 1, wherein the halogenated organic compound is a vinylic bromide.

23. The process of claim 1, wherein the hydrolytically-stable, vinylically-unsaturated precursor compound is a hydrocarbon.

24. The process of claim 1, wherein the hydrolytically-stable, vinylically-unsaturated precursor compound is ethylene.

25. The process of claim 1, wherein the hydrolytically-stable, vinylically-unsaturated precursor compound is styrene.

26. The process of claim 1, wherein the hydrolytically-stable, vinylically-unsaturated precursor compound is o-, m- or p-vinyltoluene or a mixture thereof.

27. The process of claim 1, wherein the hydrolytically-stable, vinylically-unsaturated precusor compound is o-, m- or p-divinylbenzene or a mixture thereof.

28. The process of claim 1, wherein the hydrolytically-stable, vinylically-unsaturated precursor compound contains one or more of an oxygen atom, a nitrogen atom, a sulfur atom or a phosphorus atom or a combination thereof.

29. The process of claim 1, wherein the hydrolytically-stable, vinylically-unsaturated precursor compound is acrylonitrile or methacrylonitrile.

30. The process of claim 1, wherein the hydrolytically-stable, vinylically-unsaturated precursor compound is an acrylate or methacrylate ester, wherein the alcohol moiety is alkyl of 1-30 carbon atoms or substituted or unsubstituted mono-or bicyclic aryl.

31. The process of claim 1, wherein the vinylically-unsaturated product compound is a reaction product of 4-bromobenzocyclobutene and a mixture of m-and p-vinyltoluene.

32. The process of claim 1, wherein the vinylically-unsaturated product compound is a reaction product of 4-bromobenzocyclobutene and divinylbenzene.

33. The process of claim 1, wherein the vinylically-unsaturated product compound is a reaction product of ethylene and o-bromotoluene.

34. The process of claim 1, wherein the vinylically-unsaturated product compound is a reaction product of ethylene and 4-bromobenzocyclobutene.

35. The process of claim 1, wherein the vinylically-unsaturated product compound is a reaction product of styrene and 4-bromobenzocyclobutene.

36. The process of claim 1, including a further step of treating a resulting crude product with a peroxide.

37. The process of claim 1, including a further step of chromatographing a resulting crude product over silica or alumina.

38. The process of claim 37, wherein the peroxide is aqueous hydrogen peroxide.

39. The process of claim 37, wherein the peroxide is tert-butylhydroperoxide.

40. The process of claim 1, including the further steps of treating a resulting product with a peroxide and chromatographing the thus-treated crude product over silica or alumina.

* * * * *